United States Patent [19]

Elbe et al.

[11] 4,385,061
[45] May 24, 1983

[54] COMBATING FUNGI WITH IMIDAZOLYL-VINYL KETONES AND CARBINOLS

[75] Inventors: Hans-Ludwig Elbe, Wuppertal; Karl H. Büchel, Burscheid; Paul-Ernst Frohberger, Leverkusen; Wilhelm Brandes, Leichlingen, all of Fed. Rep. of Germany

[73] Assignee: Bayer Aktiengesellschaft, Leverkusen, Fed. Rep. of Germany

[21] Appl. No.: 259,305

[22] Filed: Apr. 30, 1981

[30] Foreign Application Priority Data

May 19, 1980 [DE] Fed. Rep. of Germany ....... 3019044

[51] Int. Cl.³ .................... C07D 249/08; A01N 43/64
[52] U.S. Cl. .................... 424/273 R; 424/245; 542/440; 542/468; 542/428; 542/429; 542/455; 542/409; 548/101; 548/107; 548/341
[58] Field of Search ............ 424/273 R, 245; 548/341, 101, 107; 542/440, 468, 428, 429, 455, 469

[56] References Cited

U.S. PATENT DOCUMENTS

| | | | |
|---|---|---|---|
| 4,067,989 | 1/1978 | Shephard et al. | 548/341 |
| 4,246,020 | 1/1981 | Shephard et al. | 424/273 R |
| 4,273,776 | 6/1981 | Hoehn | 548/341 |
| 4,277,469 | 7/1981 | Worthington et al. | 542/440 |
| 4,285,722 | 8/1981 | Worthington et al. | 542/468 |

FOREIGN PATENT DOCUMENTS 2004276 3/1979 United Kingdom .

*Primary Examiner*—Arthur P. Demers
*Attorney, Agent, or Firm*—Sprung, Horn, Kramer & Woods

[57] ABSTRACT

Imidazolyl-vinyl ketones or carbinols of the formula

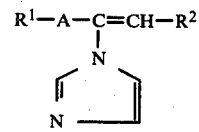

in which
A represents a keto group or a CH(OH) grouping,
$R^1$ represents an alkyl or halogenoalkyl radical and
$R^2$ represents an alkyl radical, an optionally substituted cycloalkyl or cycloalkenyl radical, a halogenoalkyl, alkoxyalkyl, alkylmercaptoalkyl, dialkylaminoalkyl or hydroxyalkyl radical, an optionally substituted alkenyl, alkinyl or alkeninyl radical, a phenylalkyl radical which is optionally substituted in the alkyl part and in the phenyl part, an optionally substituted indenyl or fluorenyl radical or an optionally substituted diphenylmethyl or triphenylmethyl radical, or acid addition products and metal salt complexes thereof which possess fungicidal activity.

10 Claims, No Drawings

COMBATING FUNGI WITH IMIDAZOLYL-VINYL KETONES AND CARBINOLS

The present invention relates to certain new imidazolyl-vinyl ketones and carbinols, to a process for their production and to their use as fungicides.

It has already been disclosed that certain 1-phenyl-2-imidazolyl-4,4-dimethyl-1-penten-3-ones have a good fungicidal activity (see DE-OS (German Published Specification) No. 2,838,847). It is also known that certain imidazolyl ethers, such as, for example, 1-(4-chlorophenoxy)-2-(4-chlorobenzyloxy)-3,3-dimethyl-1-imidazol-1-yl-butane, have fungicidal properties (see U.S. Pat. No. 4,229,459). However, the action of these compounds is not always completely satisfactory, especially when low amounts and concentrations are applied.

The present invention now provides, as new compounds, the imidazolyl-vinyl ketones and carbinols of the general formula

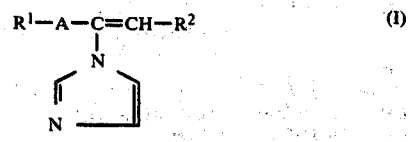

in which
A represents a keto group or a CH(OH) grouping,
$R^1$ represents an alkyl or halogenoalkyl radical
and
$R^2$ represents an alkyl radical, an optionally substituted cycloalkyl or cycloalkenyl radical, a halogenoalkyl, alkoxyalkyl, alkylmercaptoalkyl, dialkylaminoalkyl, or hydroxyalkyl radical, an optionally substituted alkenyl, alkinyl or alkeninyl radical, a phenylalkyl radical which is optionally substituted in the alkyl part and in the phenyl part, an optionally substituted indenyl or fluorenyl radical, or an optionally substituted diphenylmethyl or triphenylmethyl radical,
and physiologically acceptable acid addition salts and metal salt complexes thereof.

The compounds of the formula (I) can exist in two geometric isomer forms (E-form and Z-form), depending on the arrangement of the groups bonded to the double bond; they are preferentially obtained in a varying E/Z-isomer ratio. If A represents the CH(OH) grouping, an asymmetric carbon atom is present, so that, in this case, the compounds of the formula (I) are also obtained in two optical isomer forms; they are preferentially obtained as racemates. The present invention relates both to the individual isomers and to the isomer mixtures.

We further provide a process for the production of a compound of the present invention in which a ketoenamine of the general formula

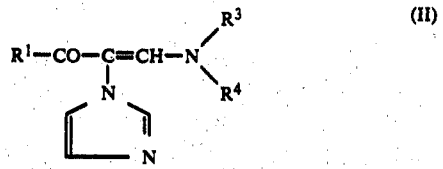

in which
$R^1$ has the abovementioned meaning and
$R^3$ and $R^4$ are identical or different and represent alkyl radicals, is reacted with an organo-magnesium compound of the general formula

in which
$R^2$ has the abovementioned meaning and
Hal represents a halogen atom, in the presence of a solvent, and, if a compound of formula (I) in which A represent a CH(OH) grouping is required, the keto derivatives of the formula (I) formed is reduced, and/or the product is converted, if desired, into a physiologically acceptable acid addition salt or metal complex thereof.

The new imidazolyl-vinyl ketones and carbinols of the present invention have powerful fungicidal properties. Surprisingly, the compounds according to the invention exhibit a better fungicidal activity than the 1-phenyl-2-imidazolyl-4,4-dimethyl-1-penten-3-ones, which are known from the state of the art and are closely related compounds chemically and from the point of view of their action, and than 1-(4-chlorophenoxy)-2-(4-chlorobenzyloxy)3,3-dimethyl-1-imidazol-1-yl-butane, which is likewise known from the state of the art and is a closely related compound from the point of view of its action. The substances according to the invention thus represent an enrichment of the art.

Particularly preferred imidazolyl-vinyl ketones and carbinols according to the present invention are those in which $R^1$ represents a straight-chain or branched alkyl radical with 1 to 6 carbon atoms or straight-chain or branched halogenoalkyl radical with 1 to 4 carbon atoms and 1 to 5 identical or different halogen atoms (such as, in particular, fluorine, chlorine and bromine atoms), $R^2$ represents a straight-chain or branched alkyl radical with 1 to 29 carbon atoms, a cycloalkyl or cycloalkenyl radical which have in each case 5 to 7 carbon atoms and in each case optionally substituted by alkyl with 1 to 4 carbon atoms, a straight-chain or branched halogenoalkyl radical with 1 to 29 (preferably 1 to 18) carbon atoms and 1 to 5 identical or different halogen atoms (such as, in particular, fluorine, chlorine and bromine atoms), an alkoxyalkyl or alkylmercaptoalkyl radical with in each case 1 to 4 carbon atoms in each alkyl part, a straight-chain or branched dialkylaminoalkyl radical with 1 to 4 carbon atoms in the alkyl radicals on the amino groups and 1 to 29 (preferably 1 to 18) carbon atoms in the alkyl part, a straight-chain or branched hydroxyalkyl radical with 1 to 29 (preferably 1 to 18) carbon atoms, an optionally substituted, straight-chain or branched alkenyl, alkinyl or alkeninyl radical with in each case up to 6 carbon atoms (substituents being selected from hydroxyl, alkoxy with 1 to 4 carbon atoms and phenyl, which is optionally substituted by halogen, such as, preferably, fluorine and chlorine, alkyl with 1 to 4 carbon atoms, alkoxy and alkylthio with in each case 1 to 4 carbon atoms, and halogenoalkoxy and halogenoalkylthio with in each case 1 to 5 identical or different halogen atoms, such as, preferably, fluorine and chlorine atoms, cyano and nitro), represents a phenylalkyl radical which has 1 to 4 carbon atoms in the alkyl part (such as, preferably, benzyl) and is optionally monosubstituted or polysubstituted by identical or different substituents (preferred substituents on the phenyl being those already mentioned above, and preferred substituents on the alkyl which may be mentioned being: cyano, hydroxycarbonyl and alkoxycarbonyl with 1 to 4 carbon atoms in the alkyl part), represents an indenyl or fluorenyl radical which is optionally substituted by halogen or alkyl or alkoxy with in each case 1 to 4 carbon atoms, or represents an optionally substituted diphenylmethyl or triphenylmethyl radical, (preferred possible substituents on the phenyl being those already mentioned above), and A has the meaning indicated above.

Particularly preferred compounds of the formula (I) are those in which $R^1$ represents a tert.-butyl, chloro-tert.-butyl, fluoro-tert.-butyl, dichloro-tert.-butyl or difluoro-tert.-butyl radical.

The following compounds of the general formula (I) may be mentioned specifically, in addition to the compounds mentioned in the preparative examples hereinbelow:

TABLE 1

$$R^1-A-\underset{\underset{N}{\overset{N}{|}}}{C}=CH-R^2 \quad (I)$$

| $R^1$ | $R^2$ | A |
|---|---|---|
| $(CH_3)_3C-$ | $-CH(C_2H_5)_2$ | CO |
| $(CH_3)_3C-$ | $-C(CH_3)_3$ | CO |
| $(CH_3)_3C-$ | $-CH_2-\phi-OCF_3$ | CO |
| $(CH_3)_3C-$ | $-CH_2-\phi-OCF_2CHFCl$ | CO |
| $(CH_3)_3C-$ | $-CH_2-CH_2-O-C_3H_7-n$ | CO |
| $(CH_3)_3C-$ | $-C_{23}H_{47}-n$ | CO |
| $(CH_3)_3C-$ | $-CH_2-CH_2-S-C_3H_7-n$ | CO |
| $(CH_3)_3C-$ | $-(CH_2)_3-N(CH_3)_2$ | CO |
| $(CH_3)_3C-$ | $-(CH_2)_7-OH$ | CO |
| $(CH_3)_3C-$ | $-C(CH_3)=CH_2$ | CO |
| $(CH_3)_3C-$ | $-C(CH_3)=C(CH_3)_2$ | CO |
| $(CH_3)_3C-$ | $-(CH_2)_7F$ | CO |
| $(CH_3)_3C-$ | $-(CH_2)_7Cl$ | CO |
| $(CH_3)_3C-$ | cyclohexenyl | CO |
| $(CH_3)_3C-$ | cyclohexenyl | CO |
| $ClCH_2-C(CH_3)_2-$ | $-C_2H_5$ | CO |
| $ClCH_2-C(CH_3)_2-$ | $-CH(CH_3)(C_2H_5)$ | CO |
| $ClCH_2-C(CH_3)_2-$ | $-C_4H_9-n$ | CO |
| $ClCH_2-C(CH_3)_2-$ | $-CH(CH_3)_2$ | CO |
| $ClCH_2-C(CH_3)_2-$ | $-C(CH_3)_3$ | CO |
| $ClCH_2-C(CH_3)_2-$ | $-\phi(H)$ | CO |
| $ClCH_2-C(CH_3)_2-$ | $-CH_2-\phi$ | CO |

TABLE 1-continued $$R^1-A-\underset{\underset{N}{\overset{N}{|}}}{C}=CH-R^2 \quad (I)$$

| $R^1$ | $R^2$ | A |
|---|---|---|
| $ClCH_2-C(CH_3)_2-$ | $-C\equiv C-\phi$ | CO |
| $FCH_2-C(CH_3)_2-$ | $-C_2H_5$ | CO |
| $FCH_2-C(CH_3)_2-$ | $-C_4H_9-n$ | CO |
| $FCH_2-C(CH_3)_2-$ | $-C(CH_3)_3$ | CO |
| $FCH_2-C(CH_3)_2-$ | $-C_7H_{15}-n$ | CO |
| $FCH_2-C(CH_3)_2-$ | $-\phi(H)$ | CO |
| $FCH_2-C(CH_3)_2-$ | $-CH_2-\phi$ | CO |
| $FCH_2-C(CH_3)_2-$ | $-C\equiv C-\phi$ | CO |
| $CH_3-C(CH_2Cl)_2-$ | $-C_2H_5$ | CO |
| $CH_3-C(CH_2Cl)_2-$ | $-CH(CH_3)(C_2H_5)$ | CO |
| $CH_3-C(CH_2Cl)_2-$ | $-C_4H_9-n$ | CO |
| $CH_3-C(CH_2Cl)_2-$ | $-CH(CH_3)_2$ | CO |
| $CH_3-C(CH_2Cl)_2-$ | $-C(CH_3)_3$ | CO |
| $CH_3-C(CH_2Cl)_2-$ | $-C_7H_{15}-n$ | CO |
| $CH_3-C(CH_2Cl)_2-$ | $-\phi(H)$ | CO |
| $CH_3-C(CH_2Cl)_2-$ | $-CH_2-\phi$ | CO |
| $CH_3-C(CH_2Cl)_2-$ | $-C\equiv C-\phi$ | CO |
| $CH_3-C(CH_2F)_2-$ | $-C_2H_5$ | CO |
| $CH_3-C(CH_2F)_2-$ | $-CH(CH_3)(C_2H_5)$ | CO |
| $CH_3-C(CH_2F)_2-$ | $-C_4H_9-n$ | CO |
| $CH_3-C(CH_2F)_2-$ | $-CH(CH_3)_2$ | CO |
| $CH_3-C(CH_2F)_2-$ | $-C(CH_3)_3$ | CO |
| $CH_3-C(CH_2F)_2-$ | $-C_7H_{15}-n$ | CO |
| $CH_3-C(CH_2F)_2-$ | $-\phi(H)$ | CO |
| $CH_3-C(CH_2F)_2-$ | $-CH_2-\phi$ | CO |
| $CH_3-C(CH_2F)_2-$ | $-C\equiv C-\phi$ | CO |
| $(CH_3)_3C-$ | $-CH(C_2H_5)_2$ | CH(OH) |
| $(CH_3)_3C-$ | $-C(CH_3)_3$ | CH(OH) |
| $(CH_3)_3C-$ | $-CH_2-\phi-OCF_3$ | CH(OH) |
| $(CH_3)_3C-$ | $-CH_2-\phi-OCF_2CHFCl$ | CH(OH) |
| $(CH_3)_3C-$ | $-CH_2-CH_2-O-C_3H_7-n$ | CH(OH) |
| $(CH_3)_3C-$ | $-C_{23}H_{47}-n$ | CH(OH) |
| $(CH_3)_3C-$ | $-CH_2-CH_2-S-C_3H_7-n$ | CH(OH) |
| $(CH_3)_3C-$ | $-(CH_2)_3-N(CH_3)_2$ | CH(OH) |

TABLE 1-continued $$R^1-A-\underset{\underset{\underset{N}{\bigvee_{N}}}{|}}{C}=CH-R^2 \quad (I)$$

| $R^1$ | $R^2$ | A |
|---|---|---|
| $(CH_3)_3C-$ | $-(CH_2)_7-OH$ | CH(OH) |
| $(CH_3)_3C-$ | $-\underset{CH_3}{\overset{}{C}}=CH_2$ | CH(OH) |
| $(CH_3)_3C-$ | $-\underset{CH_3}{\overset{}{C}}=C(CH_3)_3$ | CH(OH) |
| $(CH_3)_3C-$ | $-(CH_2)_7F$ | CH(OH) |
| $(CH_3)_3C-$ | $-(CH_2)_7Cl$ | CH(OH) |
| $(CH_3)_3C-$ | cyclohexyl | CH(OH) |
| $(CH_3)_3C-$ | cyclohexenyl | CH(OH) |
| $ClCH_2-C(CH_3)_2-$ | $-C_2H_5$ | CH(OH) |
| $ClCH_2-C(CH_3)_2-$ | $-CH(CH_3)(C_2H_5)$ | CH(OH) |
| $ClCH_2-C(CH_3)_2-$ | $-C_4H_9-n$ | CH(OH) |
| $ClCH_2-C(CH_3)_2-$ | $-CH(CH_3)_2$ | CH(OH) |
| $ClCH_2-C(CH_3)_2-$ | $-C(CH_3)_3$ | CH(OH) |
| $ClCH_2-C(CH_3)_2-$ | $-\langle H \rangle$ | CH(OH) |
| $ClCH_2-C(CH_3)_2-$ | $-CH_2-\langle\bigcirc\rangle$ | CH(OH) |
| $ClCH_2-C(CH_3)_2-$ | $-C\equiv C-\langle\bigcirc\rangle$ | CH(OH) |
| $FCH_2-C(CH_3)_2-$ | $-C_2H_5$ | CH(OH) |
| $FCH_2-C(CH_3)_2-$ | $-C_4H_9-n$ | CH(OH) |
| $FCH_2-C(CH_3)_2-$ | $-C(CH_3)_3$ | CH(OH) |
| $FCH_2-C(CH_3)_2-$ | $-C_7H_{15}-n$ | CH(OH) |
| $FCH_2-C(CH_3)_2-$ | $-\langle H \rangle$ | CH(OH) |
| $FCH_2-C(CH_3)_2-$ | $-CH_2-\langle\bigcirc\rangle$ | CH(OH) |
| $FCH_2-C(CH_3)_2-$ | $-C\equiv C-\langle\bigcirc\rangle$ | CH(OH) |
| $CH_3-C(CH_2Cl)_2-$ | $-C_2H_5$ | CH(OH) |
| $CH_3-C(CH_2Cl)_2-$ | $-CH(CH_3)(C_2H_5)$ | CH(OH) |
| $CH_3-C(CH_2Cl)_2-$ | $-C_4H_9-n$ | CH(OH) |
| $CH_3-C(CH_2Cl)_2-$ | $-CH(CH_3)_2$ | CH(OH) |
| $CH_3-C(CH_2Cl)_2-$ | $-C(CH_3)_3$ | CH(OH) |
| $CH_3-C(CH_2Cl)_2-$ | $-C_7H_{15}-n$ | CH(OH) |
| $CH_3-C(CH_2Cl)_2$ | $-\langle H \rangle$ | CH(OH) |
| $CH_3-C(CH_2Cl)_2-$ | $-CH_2-\langle\bigcirc\rangle$ | CH(OH) |
| $CH_3-C(CH_2Cl)_2-$ | $-C\equiv C-\langle\bigcirc\rangle$ | CH(OH) |
| $(CH_3)_3-C-$ | $-CH(\langle\bigcirc\rangle)_2$ | CH(OH) |
| $(CH_3)_3C-$ | $-CH(CN)-\langle\bigcirc\rangle-Cl$ | CH(OH) |

If, for example, 4,4-dimethyl-1-dimethylamino-2-imidazol-1-yl-1-penten-3-one and tert.-butyl-magnesium bromide are used as starting substances, the course of the reaction in the process according to the invention is illustrated by the following equation:

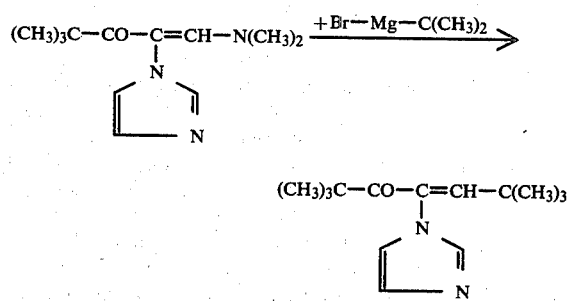

If, for example, 2,2,6,6-tetramethyl-4-(imidazol-1-yl)-3-hepten-5-one and sodium borohydride are used as starting substances, the course of the reaction in the reduction according to the invention is illustrated by the following equation:

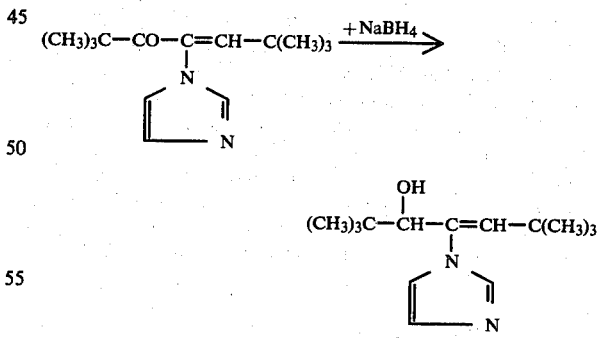

Particularly preferred keto-enamines of formula (II) to be used as starting substances for the process according to the invention are those in which $R^1$ represents those radicals which have already been mentioned for this substituent in connection with the description of the preferred and particularly preferred compounds according to the invention. $R^3$ and $R^4$ are identical or different and preferably represent alkyl with 1 to 4 carbon atoms, especially methyl.

The keto-enamines of the formula (II) are the subject of Patent Application Ser. No. 219,154, filed Dec. 22, 1980, now pending, corresponding to German Patent Application No. P 30 00643.0 of 10.1 80 [Le A 20 084]. The keto-enamines of the formula (II) can be obtained by the process described in that application, by reacting a imidazolyl-ketone of the general formula

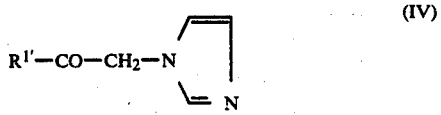

(IV)

in which $R^1$ has the abovementioned meaning, with an amide acetal or aminal ester of the general formula

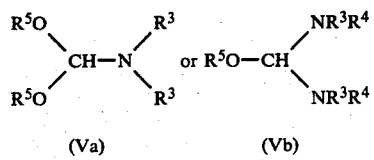

(Va) (Vb)

in which
  $R^3$ and $R^4$ have the abovementioned meaning and
  $R^5$ represents an alkyl radical with 1 to 4 carbon atoms, in a manner which is in itself known in the presence of an inert organic solvent, such as an aromatic hydrocarbon, and such as, preferably, an excess of amide acetal or aminal ester of the formula (Va) or (Vb) employed, at the boiling point (in this context, see also Chem. Ber. 101, 41–50 (1968); J. Org. Chem. 43, 4148–50 (1978) and the preparative examples hereinbelow).

The imidazolyl-ketones of the formula (IV) are known (see, for example, DE-OS (German Published Specification) No. 2,610,022 and DE-OS (German Published Specification) No. 2,638,470); they can be prepared by customary methods, by reacting the corresponding halogeno-ketones with imidazole in the presence of an acid-binding agent.

The amide acetals and aminal esters of the formulae (Va) and (Vb) are generally known compounds of organic chemistry (see for example, Chem. Ber. 101, 41–50 (1968) and J. Org. Chem. 43, 4248–50 (1978)).

Particularly preferred organo-magnesium compounds of formula (III) also to be used as starting substances for the reaction according to the invention are those in which $R^2$ represents those radicals which have already been mentioned as for this substituent in connection with the description of preferred and particularly preferred compounds according to the invention, and Hal represents a chlorine or bromine atom.

The organo-magnesium compounds of the formula (III) are generally known compounds of organic chemistry.

Preferred possible solvents for the reaction according to the invention are inert organic solvents, in pure form or as mixtures. These solvents include, preferably, ethers, such as diethyl ether, methyl ethyl ether, tetrahydrofuran or dioxane, aliphatic and aromatic hydrocarbons, such as, in particular, benzene, toluene or xylene, and hexamethylphosphoric acid triamide.

The reaction temperatures can be varied within a substantial range in carrying out the process according to the invention. In general, the reaction is carried out between −50° and +150° C., preferably between −20° and +120° C. The reaction according to the invention can be carried out in the presence of an inert gas, such as nitrogen or helium. In carrying out the process according to the invention, 1 to 1.5 moles of organo-magnesium compound of the formula (III) are preferably employed per mole of keto-enamine of the formula (II). The compounds of formula (I) are isolated in the customary manner.

The reduction according to the invention is carried out in the customary manner, for example by reaction with complex hydrides, if appropriate in the presence of a diluent, or by reaction with aluminum isopropylate in the presence of a diluent.

If complex hydrides are used, possible diluents for the reaction according to the invention are polar organic solvents. These include, preferably, alcohols, such as methanol, ethanol, butanol and isopropanol, and ethers, such as diethyl ether or tetrahydrofuran. The reaction is in general carried out at 0° to 30° C., preferably at 0° to 20° C. About 1 mole of a complex hydride, such as sodium borohydride and lithium alanate, is employed per mole of the ketone of the formula (I). In order to isolate the reduced compounds of the formula (I), the residue is taken up in dilute hydrochloric acid and the mixture is then rendered alkaline and extracted with an organic solvent. Further working up is effected in the customary manner.

If aluminum isopropylate is used, preferred possible diluents for the reaction according to the invention are alcohols, such as isopropanol, or inert hydrocarbons, such as benzene. The reaction temperatures can again be varied within a substantial range; in general, the reaction is carried out between 20° and 120° C., preferably at 50° to 100° C. For carrying out the reaction, generally 1 to 2 moles of aluminum isopropylate are employed per mole of the appropriate ketone of the formula (I). In order to isolate the reduced compounds of the formula (I), the excess solvent is removed by distillation in vacuo and the aluminum compound formed is decomposed with dilute sulphuric acid or sodium hydroxide solution. Further working up is effected in the customary manner.

The following acids can preferably be used for the preparation of physiologically acceptable acid addition salts of the compounds of the formula (I): hydrogen halide acids (such as hydrobromic acid and in particular, hydrochloric acid), phosphoric acid, nitric acid, sulphuric acid, monofunctional and bifunctional carboxylic acids and hydroxycarboxylic acids (such as acetic acid, maleic acid, succinic acid, fumaric acid, tartaric acid, citric acid, salicylic acid, sorbic acid and lactic acid) and sulphonic acids (such as p-toluenesulphonic acid and 1,5-naphthalenedisulphonic acid).

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

Salts of metals of main groups II to IV and of subgroups I and II and IV to VIII are preferably used for the preparation of metal salt complexes of the compounds of the formula (I), examples of metals which may be mentioned being copper, zinc, manganese, magnesium, tin, iron and nickel.

Possible anions of the salts are, preferably, those which are derived from the following acids: hydrogen halide acids (such as hydrochloric acid and hydrobromic acid), phosphoric acid, nitric acid and sulphuric acid.

The metal salt complexes of the compounds of the formula (I) can be obtained in a simple manner by customary processes, thus, for example, by dissolving the metal salt in alcohol, for example ethanol, and adding the solution to the compound of the formula (I). The metal salt complexes can be purified in a known manner, for example by filtration, isolation and, if appropriate, by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Asoomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used particularly successfully for combating cereal diseases, such as powdery mildew of barley or cereal (*Erysiphe graminis*) and stripe disease of barley, Venturia species, such as against the apple scab causative organism (*Fusicladium dendriticum*); Erysiphe species, such as against the powdery mildew of cucumber causative organism (*Erysiphe cichoracearum*); and for combating brown rot of tomato (*Phytophthora infestans*). It should be particularly emphasised that the active compounds according to the invention not only have a protective action but in some cases also have a systemic action. Thus, it is possible to protect plants from fungal attack when the active compound is fed to the above-ground parts of the plant via the soil and the root or via the seed.

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing injecting, forming a slurry, brushing on, dusting, scattering, dry dressing, moist dressing, wet dressing, slurry dressing or encrusing.

Especially in the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% are required at the place of action.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

Example 1

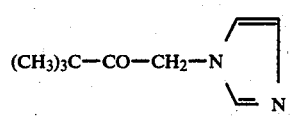

(a)

136.2 g (2 moles) of imidazole were added in portions, at room temperature, to 276.4 g (2 moles) of ground potassium carbonate and 269.2 g (2 moles) of α-chloropinacolin in 500 ml of acetone, whereupon the internal temperature rose to the boiling point. The mixture was stirred under reflux for 5 hours and then cooled to room temperature. The reaction mixture was filtered and the filtrate was concentrated by distilling off the solvent in vacuo. The oily residue was distilled. 296 g (89% of theory) of 3,3-dimethyl-1-(imidazol-1-yl)-butan-2-one of melting point ~20° C. were obtained.

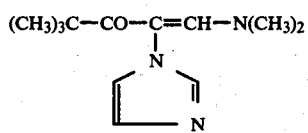

(b)

41.6 g (0.25 mole) of 3,3-dimethyl-1-(imidazol-1-yl)-butan-2-one were heated under reflux with 35.7 g (0.3 mole) of dimethylformamide dimethyl acetal for 5 hours. The excess acetal was then distilled off. The oil which remained crystallised on cooling.

50 g (90.5% of theory) of 4,4-dimethyl-1-dimethylamino-2-(imidazol-1-yl)-pent-1-en-3-one of melting point 45°–50° C. were obtained.

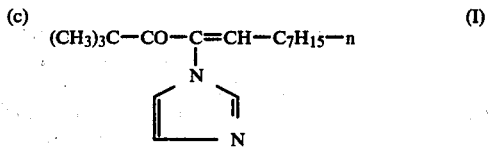

(c)    (I)

A solution of 61 g (0.3 mole) of n-heptylmagnesium bromide in 130 ml of ether was added to 55.5 g (0.25 mole) of 4,4-dimethyl-1-dimethylamino-2-(imidazol-1-yl)-pent-1-en-3-one in 800 ml of ether at −20° C. in the course of 30 minutes under an inert gas (nitrogen). When the addition had ended, the reaction mixture was allowed to warm to room temperature in the course of about 2 hours. Dilute hydrochloride acid was then added and the organic phase was separated off, washed with water, dried over sodium sulphate and concentrated. 54 g (78% of theory) of 2,2-dimethyl-4-(imidazol-1-yl)-5-dodecen-3-one with a refractive index $n_D^{20}$ of 1.4802 were obtained.

EXAMPLE 2

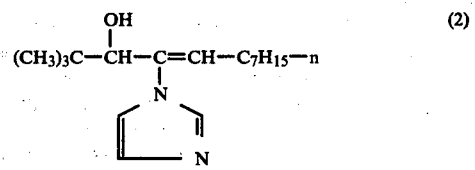

(2)

(Reduction)

1.1 g (0.029 mole) of sodium borohydride, dissolved in 10 ml of water, were added dropwise to 27.6 g (0.1 mole) of 2,2-dimethyl-4-(imidazol-1-yl)-5-dodecen-3-one (obtained as described in Example 1) in 100 ml of methanol at 0° C. When the addition had ended, the mixture was subsequently stirred at room temperature for 2 hours. Thereafter, the pH value was adjusted to 6 to 7 with dilute hydrochloric acid, the mixture was concentrated and the residue was extracted with chloroform. The organic phase was dried over sodium sulphate and concentrated. 25.6 g (92% of theory) of 2,2-dimethyl-4-(imidazol-1-yl)-5-decen-3-ol with a refractive index $n_D^{20}$ of 1.4860 were obtained.

The following compounds of the general formula (I)

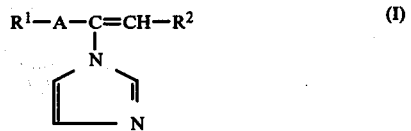

(I)

were obtained in a manner corresponding to that indicated in Examples 1 and 2:

TABLE 2

| Compound No. | $R^1$ | $R^2$ | A | Melting point (°C.) or refractive index $n_D^{20}$ |
|---|---|---|---|---|
| 3 | $(CH_3)_3C-$ | $-CH_3$ | CO | 1.5097 |
| 4 | $(CH_3)_3C-$ | $-C_2H_5$ | CO | 1.5032 |
| 5 | $(CH_3)_3C-$ | $-CH(CH_3)_2$ | CO | 1.4928 |
| 6 | $(CH_3)_3C-$ | $-C_4H_9-n$ | CO | 1.4926 |
| 7 | $(CH_3)_3C-$ | $-C(CH_3)_3$ | CO | viscous oil |

TABLE 2-continued

| Compound No. | R¹ | R² | A | Melting point (°C.) or refractive index $n_D^{20}$ |
|---|---|---|---|---|
| 8 | $(CH_3)_3C-$ | $-CH(CH_3)C_2H_5$ | CO | 30 |
| 9 | $(CH_3)_3C-$ | $-CH=CH_2$ | CO | viscous oil |
| 10 | $(CH_3)_3C-$ | —⟨cyclopentyl-H⟩ | CO | 1.5121 |
| 11 | $(CH_3)_3C-$ | —⟨cyclohexyl-H⟩ | CO | 1.5005 |
| 12 | $(CH_3)_3C-$ | $-CH_2-$⟨phenyl⟩ | CO | 1.5430 |
| 13 | $(CH_3)_3C-$ | $-C\equiv C-$⟨phenyl⟩ | CO | viscous oil |
| 14 | $(CH_3)_3C-$ | $-CH($⟨phenyl⟩$)_2$ | CO | 35–40 |
| 15 | $(CH_3)_3C-$ | $-C_8H_{17}-n$ | CO | 1.4759 |
| 16 | $(CH_3)_3C-$ | $-C_9H_{19}-n$ | CO | 1.4769 |
| 17 | $(CH_3)_3C-$ | $-C_{10}H_{21}-n$ | CO | 1.4820 |
| 18 | $(CH_3)_3C-$ | $-C_6H_{13}-n$ | CO | 1.4835 |
| 19 | $(CH_3)_3C-$ | $-C_{12}H_{25}-n$ | CO | 1.4820 |
| 20 | $FCH_2-C(CH_3)_2-$ | $-CH(CH_3)C_2H_5$ | CO | 1.4947 |
| 21 | $FCH_2-C(CH_3)_2-$ | $-CH(CH_3)_2$ | CO | 1.5100 |
| 22 | $(CH_3)_3C-$ | (methyl-fluorenyl) | CO | 186–87 |
| 23 | $(CH_3)_3C-$ | $-CH(CN)-$⟨phenyl⟩$-Cl$ | CO | 177–79 |
| 24 | $(CH_3)_3C-$ | $-CH(CH_3)_2$ | CO | 67–58 (xCuCl₂) |
| 25 | $(CH_3)_3C-$ | $-C_7H_{15}-n$ | CO | viscous oil (xCuCl₂) |
| 26 | $(CH_3)_3C-$ | $-CH_3$ | CO | 76–79 (xCuCl₂) |
| 27 | $(CH_3)_3C-$ | $-C(CH_3)_3$ | CO | 87–90 (xCuCl₂) |
| 28 | $(CH_3)_3C-$ | $-CH_2-$⟨phenyl⟩ | CO | 114–20 (xCuCl₂) |
| 29 | $(CH_3)_3C-$ | $-CH(CH_3)C_2H_5$ | CO | 60–64 (xCuCl₂) |
| 30 | $(CH_3)_3C-$ | (methyl-indenyl) | CO | 157–61 (xCuCl₂) |
| 31 | $(CH_3)_3C-$ | $-C_2H_5$ | CO | 70 (xCuCl₂) |
| 32 | $(CH_3)_3C-$ | $-C_6H_{13}-n$ | CO | viscous oil (xCuCl₂) |
| 33 | $(CH_3)_3C-$ | $-C_4H_9-n$ | CH(OH) | 1.4970 |
| 34 | $(CH_3)_3C-$ | $-CH_3$ | CH(OH) | 1.5106 |
| 35 | $(CH_3)_3C-$ | $-CH(CH_3)_2$ | CH(OH) | 1.4979 |
| 36 | $(CH_3)_3C-$ | $-CH(CH_3)C_2H_5$ | CH(OH) | 1.4966 |
| 37 | $(CH_3)_3C-$ | —⟨cyclopentyl-H⟩ | CH(OH) | 1,5100 |
| 38 | $(CH_3)_3C-$ | $-C(CH_3)_3$ | CH(OH) | 30 |
| 39 | $(CH_3)_3C-$ | $-CH_2-$⟨phenyl⟩ | CH(OH) | 117–25 |

TABLE 2-continued

| Compound No. | R¹ | R² | A | Melting point (°C.) or refractive index $n_D^{20}$ |
|---|---|---|---|---|
| 40 | $(CH_3)_3C-$ | $-C{\equiv}C-\text{C}_6\text{H}_5$ | CH(OH) | 1.5485 |
| 41 | $(CH_3)_3C-$ | (fluorenyl) | CH(OH) | 199–201 |
| 42 | $(CH_3)_3C-$ | $-C_8H_{17}-n$ | CH(OH) | 1.4875 |
| 43 | $(CH_3)_3C-$ | $-C_9H_{19}-n$ | CH(OH) | 1.4809 |
| 44 | $(CH_3)_3C-$ | $-C_{12}H_{25}-n$ | CH(OH) | 1.4860 |
| 45 | $(CH_3)_3C-$ | $-C_6H_{21}-n$ | CH(OH) | 1.4837 |
| 46 | $(CH_3)_3C-$ | $-C_6H_{11}$ | CH(OH) | 1.5100 |
| 47 | $(CH_3)_3C-$ | $-C_2H_5$ | CH(OH) | 1.5120 |
| 48 | $(CH_3)_3C-$ | $-C_{10}H_{21}-n$ | CH(OH) | 1.4800 |
| 49 | $(CH_3)_3C-$ | $-C_{18}H_{37}-n$ | CO | oil |
| 50 | $(CH_3)_3C-$ | $-CH_2-CH(CH_3)_2$ | CH(OH) | 1.4925 |
| 51 | $(CH_3)_3C-$ | $-CH_2CH_2CH(CH_3)_2$ | CH(OH) | 1.4875 |
| 52 | $CH_3-C(CH_2F)_2-$ | $CH_3$ | CH(OH) | 25 |
| 53 | $CH_3-C(CH_2F)_2-$ | $-CH(CH_3)-C_2H_5$ | CH(OH) | oil |
| 54 | $(CH_3)_3C-$ | $-CH_2-CH(CH_3)_2$ | CO | 1.4937 |
| 55 | $(CH_3)_3C-$ | $-CH_2CH_2CH(CH_3)_2$ | CO | 1.4893 |
| 56 | $CH_3-C(CH_2F)_2-$ | $-CH(CH_3)-C_2H_5$ | CO | oil |
| 57 | $CH_3-C(CH_2F)_2-$ | $CH_3$ | CO | oil |
| 58 | $CH_3-C(CH_2F)_2-$ | $-CH(CH_3)_2$ | CO | oil |

The fungicidal activity of the compounds of this invention is illustrated by the following biological examples wherein the compounds according to the present invention are each identified by the number (given in brackets) from the preparative examples and Table 2 hereinabove.

The known comparison compounds are identified as follows:

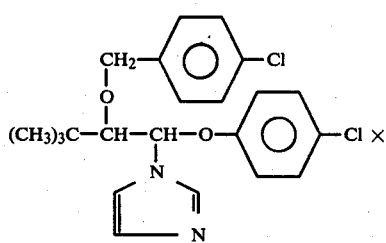

(A)

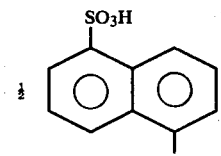

(B)

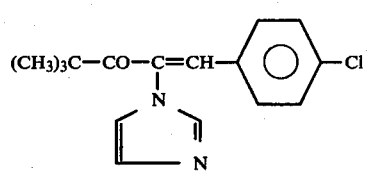

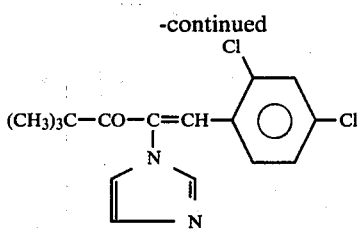

(C)

EXAMPLE 3

Erysiphe test (barley)/protective
Solvent: 100 parts by weight of dimethylformamide
Emulsifier: 0.25 part by weight of alkylaryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dew-moist. After the spray coating had dried on, the plants were dusted with spores of *Erysiphe graminis* f.sp. *hordei*.

The plants were placed in a greenhouse at a temperature of about 20° C. and a relative atmospheric humidity of about 80%, in order to promote the development of powdery mildew pustules.

Evaluation was carried out 7 days after the inoculation.

The results obtained were as follows:

TABLE 3

Erysiphe test (barley)/protective

| Active compound | Active compound concentration in the spray liquor in % by weight | Disease infestation in % of the untreated control |
|---|---|---|
| (A) (known) | 0.025 | 48.8 |
| (6) | 0.025 | 0.0 |
| (11) | 0.025 | 8.8 |
| (12) | 0.025 | 0.0 |
| (8) | 0.025 | 12.5 |
| (1) | 0.025 | 12.5 |
| (10) | 0.025 | 0.0 |
| (13) | 0.025 | 0.0 |
| (24) | 0.025 | 0.0 |
| (27) | 0.025 | 16.3 |
| (29) | 0.025 | 0.0 |
| (33) | 0.025 | 0.0 |
| (35) | 0.025 | 16.3 |
| (39) | 0.025 | 0.0 |
| (46) | 0.025 | 0.0 |
| (36) | 0.025 | 0.0 |
| (2) | 0.025 | 0.0 |
| (38) | 0.025 | 0.0 |
| (37) | 0.025 | 0.0 |
| (40) | 0.025 | 0.0 |

EXAMPLE 4

Powdery mildew of barley test (*Erysiphe graminis* var. *hordei*)/systemic (fungal disease of cereal shoots)

The active compounds were used as pulverulent seed treatment agents. These were produced by extending the active compound with a mixture of equal parts by weight of talc and kieselguhr to give a finely pulverulent mixture of the desired concentration of active compound.

For the treatment of seed, barley seed was shaken with the extended active compound in a closed glass bottle. The seed was sown at the rate of 3 × 12 grains in flowerpots, 2 cm deep in a mixture of one part by volume of Fruhstorfer standard soil and one part by volume of quartz sand. The germination and emergence took place under favourable conditions in a greenhouse. 7 days after sowing, when the barley plants had unfolded their first leaf, they were dusted with fresh spores of *Erysiphe graminis* var. *hordei* and grown on at 21° to 22° C. and 80 to 90% relative atmospheric humidity and 16 hours' exposure to light. The typical mildew pustules formed on the leaves within 6 days.

The degree of infection was expressed as a percentage of the infection of the untreated control plants. Thus, 0% denoted no infection and 100% denoted the same degree of infection as in the case of the untreated control. The more active the compound, the lower was the degree the mildew infection.

The results obtained were as follows:

TABLE 4

Powdery mildew of barley test (*Erysiphe graminis* var. hordei)/systemic

| Active Compounds | Active compound concentration in the dressing in % by weight | Amount of dressing applied in g/kg of seed | Infection in % of untreated control |
|---|---|---|---|
| (A) (known) | 25 | 10 | 100 |
| (46) | 25 | 4 | 12.5 |

EXAMPLE 5

Erysiphe test (cucumbers)/protective
Solvent: 4.7 parts by weight of acetone
Emulsifier: 0.3 part by weight of alkylaryl polyglycol ether
Water: 95.0 parts by weight The amount of active compound required for the desired concentration of active compound in the spray liquid was mixed with the stated amount of solvent, and the concentrate was diluted with the stated amount of water which contained the stated additions.

Young cucumber plants with about three foliage leaves were sprayed with the spray liquid until dripping wet. The cucumber plants remained in a greenhouse for 24 hours to dry. They were then, for the purpose of inoculation, dusted with conidia of the fungus *Erysiphe cichoracearum*. The plants were subsequently placed in a greenhouse at 23° to 24° C. and at a relative atmospheric humidity of about 75%.

After 12 days, the infection of the cucumber plants was determined. The assessment data were converted to percent infection. 0% denoted no infection and 100% meant that the plants were totally infected.

The results obtained were as follows:

TABLE 5

Erysiphe test (cucumbers)/protective

| Active compound | Infection in % at an active compound concentration of 0.0005% |
|---|---|
| (B) | 84 |
| (C) | 100 |
| (33) | 37 |
| (46) | 37 |

EXAMPLE 6

Phytophthora test (tomatoes)/protective
Solvent: 4.7 parts by weight of acetone
Emulsifier: 0.3 part by weight of alkylaryl polyglycol ether
Water: 95.0 parts by weight The amount of active compound required for the desired concentration of the active compound in the spray liquid was mixed with the stated amount of solvent and the concentrate was diluted with the stated amount of water which contained the stated additions.

Young tomato plants with 2 to 4 foliage leaves were sprayed with the spray liquid until dripping wet. The plants remained in a greenhouse for 24 hours at 20° C. and at a relative atmospheric humidity of 70%. The tomato plants were then inoculated with an aqueous spore suspension of *Phytophthora infestans*. The plants were brought into a humidity chamber with an atmospheric humidity of 100% and a temperature of 18° to 20° C.

After 5 days the infection of the tomato plants was determined. The assessment data were converted to percent infection: 0% denoted no infection and 100% denoted that the plants were totally infected.

The results obtained were as follows:

TABLE 6

Phytophthora test (tomatoes)/protective

| Active compound | Infection in % at an active compound concentration of 0.005% |
|---|---|
| (B) (known) | 21 |
| (26) | 2 |
| (27) | 4 |
| (28) | 0 |

TABLE 6-continued

| Phytophthora test (tomatoes)/protective | |
|---|---|
| Active compound | Infection in % at an active compound concentration of 0.005% |
| (29) | 2 |

It will be understood that the specification and examples are illustrative but not limitative of the present invention and that other embodiments within the spirit and scope of the invention will suggest themselves to those skilled in the art.

We claim:

1. An imidazolyl-vinyl ketone or carbinol of the formula

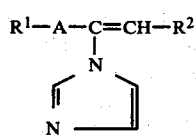

in which

A is a keto group or a CH(OH) grouping, $R^1$ is an alkyl radical with 1 to 6 carbon atoms or a halogenoalkyl radical with 1 to 4 carbon atoms and 1 to 5 identical or different halogen atoms, $R^2$ is an alkyl radical with 1 to 29 carbon atoms, a cycloalkyl or cycloalkenyl radical which have in each case 5 to 7 carbon atoms and in each case optionally substituted by alkyl with 1 to 4 carbon atoms, a halogenoalkyl radical with 1 to 29 carbon atoms and 1 to 5 identical or different halogen atoms, an alkoxyalkyl or alkylmercaptoalkyl radical with in each case 1 to 4 carbon atoms in each alkyl part, a dialkylaminoalkyl radical with 1 to 4 carbon atoms in the alkyl radicals on the amino groups and 1 to 29 carbon atoms in the alkyl part, HO-(CH$_2$)$_7$, an alkenyl, alkinyl or alkeninyl radical with in each case up to 6 carbon atoms, a phenylalkyl radical which has 1 to 4 carbon atoms in the alkyl part, an indenyl or fluorenyl radical which is optionally substituted by halogen or alkyl or alkoxy with in each case 1 to 4 carbon atoms, or a diphenylmethyl or triphenylmethyl radical, or an addition product thereof with a physiologically acceptable acid or a metal salt.

2. A compound according to claim 1, in which $R^1$ is a tert.-butyl, chloro-tert.-butyl, fluoro-tert.-butyl, dichloro-tert.-butyl or difluoro-tert.-butyl radical, or an addition product thereof with a hydrogen halide acid, phosphoric acid, nitric acid, sulphuric acid, a monofunctional or bifunctional carboxylic acid or hydroxycarboxylic acid or a sulphonic acid, or with a metal salt in which the metal is copper, zinc, manganese, magnesium, tin, iron or nickel and the anion is derived from hydrochloric, hydrobromic, phosphoric, nitric or sulphuric acid.

3. A compound or addition product thereof according to claim 1, wherein such compound is 2,2-dimethyl-4-(imidazol-1-yl)-7-phenyl-hept-4-en-6-in-3-one of the formula

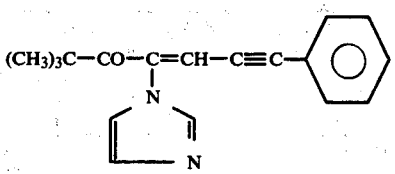

4. A compound or addition product thereof according to claim 1, wherein such compound is 2,2-dimethyl-4-(imidazol-1-yl)-hex-4-en-3-one of the formula

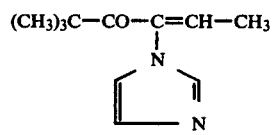

5. A compound or addition product thereof according to claim 1, wherein such compound is 2,2-dimethyl-4-(imidazol-1-yl)-6-phenyl-hex-4-en-3-one of the formula

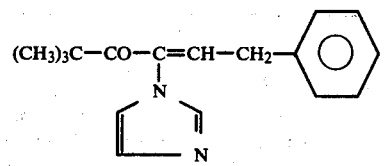

6. A compound or addition product thereof according to claim 1, wherein such compound is 2,2,6,6-tetramethyl-4-(imidazol-1-yl)-hept-4-en-3-ol of the formula

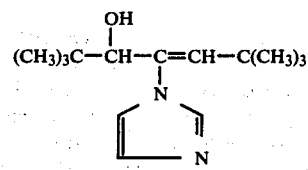

7. A compound or addition product thereof according to claim 1, wherein such compound is 2,2-dimethyl-4-(imidazol-1-yl)-5-cyclohexyl-pent-4-en-3-ol of the formula

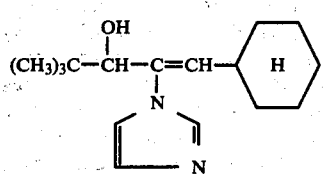

8. A fungicidal composition comprising a fungicidally effective amount of a compound or addition product according to claim 1 in admixture with a diluent.

9. A method of combating fungi comprising applying to the fungi, or to a habitat thereof, a fungicidally effective amount of a compound or addition product according to claim 1.

10. The method according to claim 9, wherein such compound is 2,2-dimethyl-4-(imidazol-1-yl)-7-phenyl-hept-4-en-6-in-3-one,
2,2-dimethyl-4-(imidazol-1-yl)-hex-4-en-3-one,
2,2-dimethyl-4-(imidazol-1-yl)-6-phenyl-hex-4-en-3-one,
2,2,6,6-tetramethyl-4-(imidazol-1-yl)-hept-4-en-3-ol, or
2,2-dimethyl-4-(imidazol-1-yl)-5-cyclohexyl-pent-4-en-3-ol, or an addition product thereof with a physiologically acceptable acid or a metal salt.

* * * * *